United States Patent [19]
Wineland

[11] 4,432,352
[45] Feb. 21, 1984

[54] CERVICAL TRACTION KIT

[76] Inventor: Richard D. Wineland, 500 E. Olive Ave., Burbank, Calif. 91501

[21] Appl. No.: 354,921

[22] Filed: Mar. 8, 1982

[51] Int. Cl.[3] .................................................. A61B 1/32
[52] U.S. Cl. ........................................ 128/17; 128/321
[58] Field of Search ................... 128/1.2, 3, 17–20, 128/321–324, 345, 354

[56] References Cited

U.S. PATENT DOCUMENTS

| | | | |
|---|---|---|---|
| 2,082,782 | 6/1937 | Allen | 128/17 |
| 2,809,628 | 10/1957 | Jones | 128/17 |
| 2,858,826 | 11/1958 | Kahn | 128/17 |
| 3,320,948 | 5/1967 | Martin | 128/17 |
| 3,513,835 | 5/1970 | Ceuster | 128/12 |
| 3,789,829 | 2/1974 | Hasson | 128/1.2 |
| 3,815,609 | 6/1974 | Chester | 128/321 |
| 4,323,057 | 4/1982 | Jamieson | 128/17 |

FOREIGN PATENT DOCUMENTS 2730164  8/1978  Fed. Rep. of Germany ........ 128/20

*Primary Examiner*—Edward M. Coven
*Assistant Examiner*—Max F. Hindenburg
*Attorney, Agent, or Firm*—Sellers and Brace

[57] ABSTRACT

Disclosed is a cervical traction kit including a speculum and a tenaculum, both modified, cooperating to place the cervix firmly positioned in traction centrally between the speculum blades to facilitate accurate biopsy, examination and treatment. The upper speculum blade is somewhat shorter than the other and its opposite ends are slotted and shaped to support the tenaculum firmly and adjustably while holding the cervix captive and in traction.

9 Claims, 3 Drawing Figures

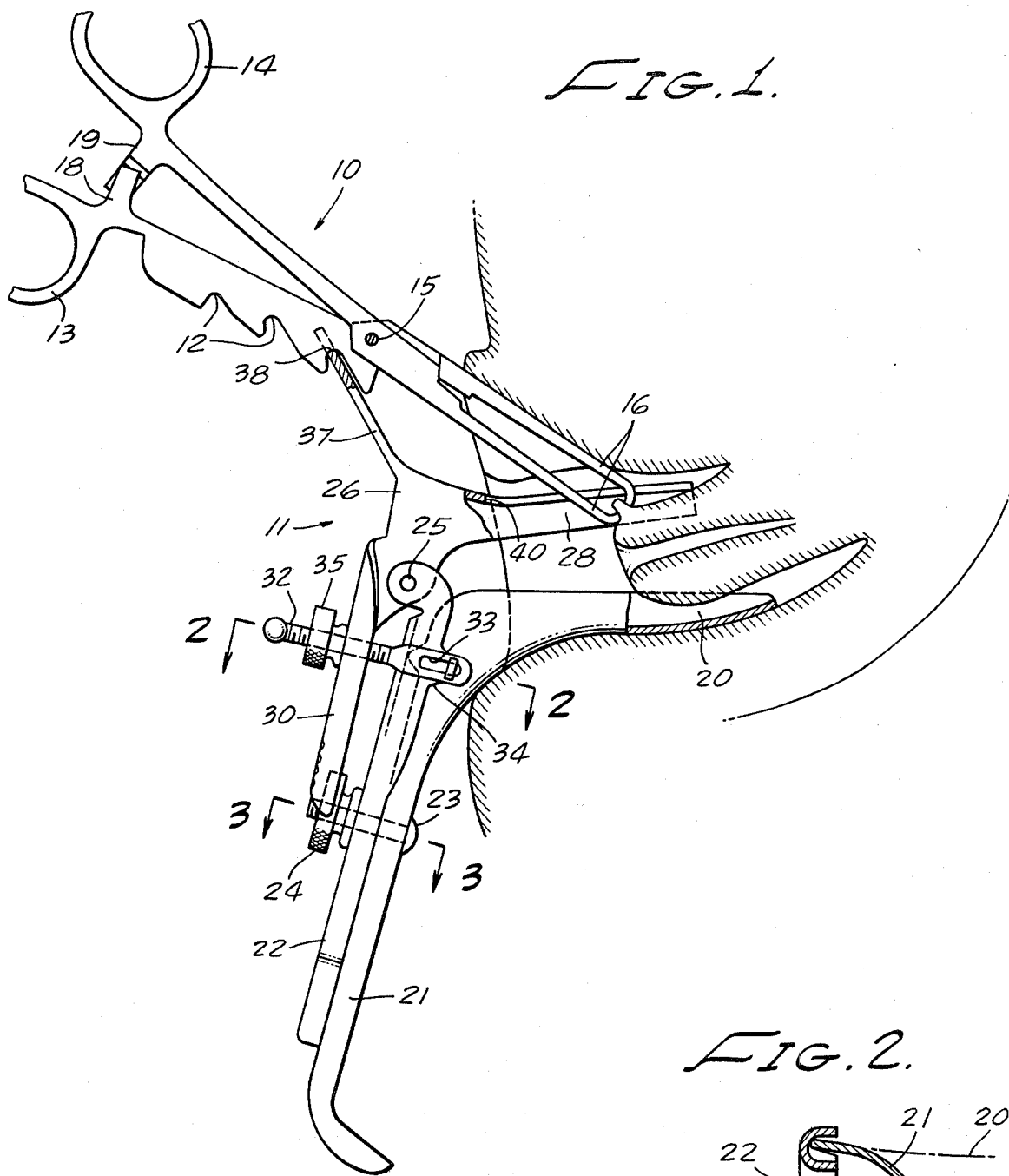

CERVICAL TRACTION KIT

This invention relates to surgical instruments, and more particularly to a unique tenaculum designed for use with a novel speculum to facilitate and expedite diagnostic and treatment procedures of the cervix and its environs.

BACKGROUND OF THE INVENTION

The inspection, treatment and performance of surgical procedures on the vaginal cavity continue to present perplexing problems not satisfactorily resolved by prior teachings and instrumentation. More particularly, problems are encountered in inspecting and treating the cervix owing to the widely varying conditions of the cervix depending upon whether the patient is parous or nulliparous. If the patient is parous, the uterus may be descensus to between a slight and an extreme degree, thereby presenting the physician with widely varying degrees of difficulties and problems, particularly as respects taking a biopsy and more particularly in safely treating cancerous condition by radiation or the like. These and other procedures have need for reliable and foolproof means providing maximum unobstructed access to the vaginal cavity but reliable on dependable means for holding the cervix firmly captive in the most advantageous position.

Prior proposals have been made in furtherance of these and other related objectives and are to be found in U.S. Patents to Kahn No. 2,858,826; Martin No. 3,320.948 and Hasson No. 3,789,829. Kahn proposes the use of a tenaculum in combination with a speculum supported independently of one another and by means of a pedestal anchored to the examination table and in a position seriously obstructing the view and procedures conducted longitudinally of the open speculum. Martin also proposes means for using a tenaculum in association with a speculum but his equipment is subject to the same limitations and shortcomings as Kahn. Hasson discloses only a radium applicator mounted in a special support permanently attached to a speculum and devoid of any means for holding the certix captive relative to the applicator.

SUMMARY OF THE INVENTION

The foregoing and other shortcomings of prior teachings are obviated by the present invention which comprises a kit, including as principal components, a modified speculum and a modified tenaculum designed for mutual cooperation in supporting the cervix most advantageously in traction by interlocked portions of these two instruments when the speculum is expanded against the walls of the vaginal cavity. For these purposes, the tenaculum is provided with a series of notches a selected one of which is engageable with detent means carried on the upturned outer end of the upper speculum blade. While so supported, the tenaculum is anchored against rotary or lateral movement since its jaws are disposed in a slot of the upper speculum blade. By this means the cervix is securely held in traction centrally of the unobstructed space between the speculum blades and is freely accessible for any of a variety of surgical procedures and treatments.

Accordingly, it is a primary object of the invention to provide a unique kit of surgical instruments useful in treating the cervix.

Another object of the invention is the provision of an improved set of speculum and the tenaculum instruments designed for mutual cooperative action in supporting the cervix in traction in a freely accessible and unobstructed area of the vaginal cavity.

Another object of the invention is the provision of an improved speculum having a relatively short upper blade and slotter at its opposite ends to support a tenaculum adjustably in a firm and stable position.

Another object of the invention is the provision of an improved tenaculum provided with a series of notches along the length thereof any one of which is engageable with detent means carried by a surgical instrument designed for use therewith.

These and other more specific objects will appear upon reading the following specification and claims and upon considering in connection therewith the attached drawing to which they relate.

Referring now to the drawing in which a preferred embodiment of the invention is illustrated:

FIG. 1 is a diagrammatic view showing my improved kit of surgical instruments in use to support a cervix in traction;

FIG. 2 is a cross sectional view on an enlarged scale taken along line 2—2 on FIG. 1; and FIG. 3 is a cross sectional view taken along line 3—3 on FIG. 1.

Referring initially to FIG. 1, there is shown an illustrative embodiment of the invention cervical traction kit comprising a modified tenaculum captively supported lengthwise of the upper blade of a surgical instrument such as a Graves type speculum 11. Tenaculum 10 is of generally conventional construction except for a series of deep V-shaped notches 12 distributed lengthwise of one of its handles. Its handles 13 and 14 are pivotally connected by pivot screw 15 and terminate in gripping jaws 16. A pair of tooth-equipped tangs 18 and 19 project toward one another in overlapping interlocking fashion from the two handles, as is well known to persons skilled in the surgical instrument art.

Speculum 11 has a generally conventional transversely-arched lower blade 20 having its outer end integral with a downwardly inclined handgrip 21. Slidably supported along this handgrip is an inverted L-shaped bracket 22 provided lengthwise thereof with a slot through which a clamping bolt 23 extends having a thumb nut 24 on its outer end. The upper end of bracket 22 is bifurcated and pivoted on shouldered rivets 25 to the downturned opposite side flanges 26 of an upper blade 28 which is somewhat shorter than lower blade 20. One of the side flanges 26 has an extension 30 having an opening 31 (FIG. 2) loosely accommodating a threaded shank 32 the slotted end 33 of which is loosely coupled to a bracket 34 of bracket 22. Threaded shank 32 is provided with a thumb nut 35 bearing against the outer surface of extension 30 attached to the upper blade 28.

The outer or rear end 37 of speculum blade 28 extends upwardly and is notched at 38 to seat any selected one of the tenaculum teeth 12. Likewise the forward end of blade 28 is provided, as is clearly shown in FIG. 1 with a long open-ended relatively narrow slot 40 sized to loosely accomodate the jaws 16 of the tenaculum. It will therefore be understood that slots 38 and 40 cooperate with one another and with adjacent portions of the tenaculum to support the latter instrument in an upright plane and against tilting in either lateral direction.

In use, the physician customarily will employ a standard speculum to expand the vaginal cavity. This having been done, he inserts the jaws of tenaculum 10 past one exterior side of the installed standard speculum and through the gap between its open blades. He then normally engages the anterior lip of the cervix between jaws 16 of tenaculum 10 following which he removes the standard speculum. The physician will shift tenaculum 10 to the 12 o'clock position and insert speculum 11 with thumb nut 35 loosened sufficiently to permit upper blade 28 to collapse toward lower blade 20. The tenaculum jaws 16 are guided into slot 40 of blade 28 as thumb nut 35 is tightened appropriately to open the two blades 20 and 28 to a comfortable position. Tenaculum 10 is then adjusted lengthwise to seat a selected one of its teeth 12 in notch 38 at the outer end 37 of instrument 11 found to position the cervix firmly in traction centrally of the area between blades 20 and 28. Thereafter, the physician proceeds to take a biopsy or to perform any of a wide variety of procedures well known to those skilled in the medical arts.

While the particular cervical traction kit herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A speculum comprising:
    first and second elongated blades extending lengthwise of one another each having a forward and a rear end and including means interconnecting the same for movement of the forward ends thereof toward and away from one another, said second blade being substantially shorter than said first blade and having a slot extending lengthwise thereof and opening through the forward end of said second blade;
    the rear ends of said blades including handgrip means manipulatable to move said blades relative to one another; and
    means on said second blade adapted to engage a tenaculum and support the same in an inclined position relative to and lengthwise of said second blade with the tenaculum jaws extending through said slot and generally into the space between the forward ends of said first and second blades.

2. A speculum as defined in claim 1 characterized in that the rear end of said second blade extends outwardly away from the rear end of said first blade, and the means on said second blade adapted to engage and support the midlength portion of a tenaculum is notched.

3. A speculum as defined in claim 1 characterized in that the rear ends of said first and second blades extend outwardly away from one another; and means on the rear end of said blade and generally parallel to said outwarding extending end of said first blade to form a portion of manipulative handgrip means for said speculum operable to open said blades.

4. A speculum as defined in claim 3 characterized in the provision of blade adjusting means controlled by thumb nut means manipulatable to secure said first and second blades in a selected open position.

5. A cervical traction kit comprising:
    a speculum having first and second elongated blades extending generally parallel to one another and each having a forward end and a rear end and including means movably interconnecting the same rearwardly of their forward ends;
    said second blade being shorter than said first blade and having a passage opening through its forward end to accomodate the insertion therethrough of the jaws of a tenaculum, said second blade having tenaculum support means;
    means manipulatable to open and maintain the forward ends of said blades apart; and
    a tenaculum having a pair of movably connected jaws and means along the midlength thereof engageable with said support means on said speculum and cooperating therewith to support said tenaculum thereon with the tenaculum jaws extending through the passage in said second blade and into the space between the forward ends of said blades.

6. A cervical traction kit as defined in claim 5 characterized in that said tenaculum and said speculum include means for supporting said tenaculum in any one of a plurality of different positions.

7. A cervical traction kit as defined in claim 6 characterized in that said tenaculum supporting means comprises a series of notches distributed along the midlength thereof.

8. That method of supporting the cervix in a stabilized position for inspection, treatment and surgical procedures by utilizing a speculum to expand the vagina while using a tenaculum to grip the cervix which method comprises:
    inserting into the vaginal cavity a speculum having a first relatively long blade and a relatively short second blade movably interconnected between the forward and rear ends thereof, providing said second blade with an elongated slot extending lengthwise thereof and opening through the forward end thereof which slot is sized to accomodate the forward end portion of said tenaculum therein while said tenaculum is in use to service a patient's cervix;
    expanding said tenaculum to stabilize the same; and
    engaging said tenaculum with a cooperating seat therefor on said speculum thereby to maintain the cervix in a desired stable position for inspection, treatment, biopsy and the like.

9. In a tenaculum of a generally conventional type having a pair of elongated blades movably interconnected between the forward and rear ends thereof which rear ends include respective finger manipulatable handles and a pair of tooth-equipped interlockable tangs and which forward ends have juxtaposed flesh gripping jaws lockable in a desired flesh-gripping position by said interlockable tangs, that inprovement which comprises:
    a row of deep V-shaped notches supported along the exterior of one of said elongated blades and adapted to seat on a generally stably-supported surgical instrument equipped with detent means thereby to support said tenaculum in a stable position on said surgical instrument while said jaws are closed against the flesh of a patient.

* * * * *